(12) United States Patent
Kasuga et al.

(10) Patent No.: US 6,458,740 B2
(45) Date of Patent: Oct. 1, 2002

(54) METHOD FOR PREPARING HETEROPOLYACID CATALYST AND METHOD FOR PRODUCING METHACRYLIC ACID

(75) Inventors: Hiroto Kasuga, Himeji; Kaori Nakatani, Takasago; Eiichi Shiraishi, Himeji, all of (JP)

(73) Assignee: Nippon Shokubai Co Ltd, Osaka (JP)

( * ) Notice: Subject to any disclaimer, the term of this patent is extended or adjusted under 35 U.S.C. 154(b) by 0 days.

(21) Appl. No.: 09/797,683

(22) Filed: Mar. 5, 2001

(30) Foreign Application Priority Data

Mar. 7, 2000 (JP) ........................................ 2000-062225

(51) Int. Cl.[7] ........................... B01J 27/19; B01J 31/00; B01J 21/02; B01J 27/198
(52) U.S. Cl. ........................ 502/211; 502/167; 502/200; 502/209
(58) Field of Search ................................ 502/167, 200, 502/209, 211

(56) References Cited

U.S. PATENT DOCUMENTS

| 4,419,270 A | 12/1983 | Ueshima | 502/209 |
| 4,558,028 A | * 12/1985 | Tsuneki et al. | 502/211 |
| 4,621,155 A | 11/1986 | Ueshima | 562/534 |

FOREIGN PATENT DOCUMENTS

| EP | 0064371 | 11/1982 |
| FR | 1601082 | 8/1970 |
| JP | 53049234 | 5/1978 |
| JP | 57012830 | 1/1982 |
| JP | 57171444 | 10/1982 |
| JP | 57177347 | 11/1982 |
| JP | 57171443 | 10/1992 |

* cited by examiner

Primary Examiner—Mark L. Bell
Assistant Examiner—Patricia L. Hailey
(74) Attorney, Agent, or Firm—Sherman & Shalloway

(57) ABSTRACT

A novel method for preparing a heteropolyacid catalyst containing a heteropolyacid composed of molybdophosphoric acid and/or molybdovanadophosphoric acid, or a salt of the heteropolyacid, is provided. The method comprises preparing an aqueous solution or aqueous dispersion which (1) contains the nitrogen-containing heterocyclic compound, nitrate anions and ammonium ions, (2) the ammonium ion content not exceeding 1.7 mols per mol of the nitrate anion content, and (3) the ammonium ion content not exceeding 10 mols per 12 mols of the molybdenum atom content by mixing raw materials containing the catalyst-constituting elements with the nitrogen-containing heterocyclic compound in the presence of water, drying and calcining the same. This heteropolyacid catalyst excels over conventional catalysts in performance, life and strength.

10 Claims, No Drawings

METHOD FOR PREPARING HETEROPOLYACID CATALYST AND METHOD FOR PRODUCING METHACRYLIC ACID

TECHNICAL FIELD TO WHICH THE INVENTION BELONGS

This invention relates to a method for preparing heteropolyacid catalyst and method for producing methacrylic acid. More particularly, the invention relates to a method for preparing heteropolyacid catalyst containing heteropolyacid formed of molybdophosphoric acid and/or molybdovanadophosphoric acid, or a salt of the heteropolyacid, which is suitable for use in preparation of unsaturated carboxylic acid through vapor phase oxidation of unsaturated aldehyde; and also to a method for producing methacrylic acid through vapor phase oxidation or vapor phase oxydehydrogenation of methacrolein, isobutyl aldehyde and/or isobutyric acid in the presence of said heteropolyacid catalyst.

Prior Art

It is well known to use heteropolyacid catalyst whose chief component is a heteropolyacid composed of phosphorus-molybdenum or phosphorus-molybdenum-vanadium, or a salt thereof, for producing methacrylic acid through vapor phase oxidation of methacrolein, isobutyl aldehyde and/or isobutyric acid.

Concerning preparation of heteropolyacid catalysts, various methods have been proposed. For example, Official Gazettes of Sho 57(1982)-12830A, Sho 57-171443A, Sho 57-171444A and Sho 57-177347A teach that preparation of heteropolyacid catalyst in the presence of a nitrogen-containing heterocyclic compound improves the catalytic performance. Specifically, in those prior art heteropolyacid catalysts are prepared by dissolving or dispersing a nitrogen-containing heterocyclic compound in water together with raw materials containing such constituent elements as phosphorus, molybdenum, vanadium and the like, concentrating the solution or dispersion under thorough stirring, drying the concentrate and calcining the same.

Problems to be solved by the Invention

Those heteropolyacid catalysts which are prepared in the presence of a nitrogen-containing heterocyclic compound, however, are inferior in selectivity and activity for reaction and in catalytic life, compared to oxidation catalysts conventionally used for making acrylic acid from acrolein, where they are used, for example, in production of methacrylic acid from methacrolein, isobutyl aldehyde and/or isobutyric acid. In consequence, those heteropolyacid catalysts must be used in large quantities and brings about rise in production costs.

An object of the present invention, therefore, is to provide a method for preparing heteropolyacid catalyst excelling in performance, life and furthermore in strength which is of particular importance for industrial use, over those heteropolyacid catalysts which are prepared by the conventional method.

Another object of the invention is to provide a method for producing methacrylic acid through vapor phase oxidation or vapor phase oxydehydrogenation of methacrolein, isobutyl aldehyde and/or isobutyric acid, using a catalyst prepared in accordance with the novel method of the invention.

Means to solve the Problems

We have discovered that the above objects can be accomplished by adjusting, in the occasion of preparing a solution or dispersion of raw materials, which contain the elements constituting the intended heteropolyacid catalyst, and a nitrogen-containing heterocyclic acid in water, the ammonium ion content and nitrate anion content of said solution or dispersion to fall within specific ranges. This invention is completed based on this knowledge.

According to the invention, thus a method for preparing a heteropolyacid catalyst containing a heteropolyacid composed of molybdophosphoric acid and/or molybdovanadophosphoric acid, or a salt of the heteropolyacid in the presence of a nitrogen-containing heterocyclic compound is provided, which method comprises preparing an aqueous solution or aqueous dispersion which (1) contains the nitrogen-containing heterocyclic compound, nitrate anions and ammonium ions, (2) the ammonium ion content not exceeding 1.7 mols per mol of the nitrate anion content, and (3) the ammonium ion content not exceeding 10 mols per 12 mols of the molybdenum atom content, by mixing raw materials containing the catalyst-constituting elements with a nitrogen-containing heterocyclic compound in the presence of water, then drying and calcining the same.

Again according to the present invention, a method for producing methacrylic acid is provided, which method comprises vapor-phase oxidation or oxydehydrogenation of methacrolein, isobutyl aldehyde and/or isobutyric acid, characterized in that a heteropolyacid catalyst which is obtained by the above-described method is used as the catalyst.

Embodiments of the Invention

The method of the invention comprises dissolving or uniformly dispersing the raw materials containing the heteropolyacid catalyst-constituting elements such as phosphorus, molybdenum, vanadium and the like and a nitrogen-containing heterocyclic compound in water, concentrating the resultant aqueous solution or dispersion, drying the concentrate and calcining the same. The characteristic feature of the invention resides in that the nitrogen-containing heterocyclic compound, ammonium ions and nitrate anions are present in said aqueous solution or dispersion, and in that the ammonium ion content and nitrate anion content are adjusted to fall within the earlier-specified ranges. It is whereby made possible to prepare a heteropolyacid catalyst excelling in performance, life and strength.

According to the method of the invention, it is possible to prepare any heteropolyacid catalyst, as long as it contains a heteropolyacid composed of molybdophosphoric acid and/or molybdovanadophosphoric acid or a salt of such heteropolyacid. The heteropolyacid catalyst, for example, can be expressed by the following general formula:

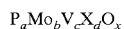

$P_a Mo_b V_c X_d O_x$ (wherein P, Mo and V are phosphorus, molybdenum and vanadium, respectively; X represents at least one metal element capable of constituting a heteropolyacid salt, which is selected from alkali metals (potassium, rubidium, cesium and the like), alkaline earth metals, copper, silver, zirconium, niobium, zinc, magnesium, selenium, tellurium, arsenic, antimony, germanium, iron, nickel and silicon; O is oxygen, a, b, c, d and x signify atomic ratios of P, Mo, V, X and O, respectively, where b is 12, a is 0.1–3, c is 0–6, d is 0.05–5, and x is a numerical value determined by valency of each element).

As nitrogen-containing heterocyclic compound, any of those known may be used. For example, pyridine, piperidine, piperazine, pyrimidine, quinoline, isoquinoline and alkyl derivatives of the foregoing may be named. Use of these compounds in the form of inorganic salts such as nitrate, sulfate, chloride and the like is recommended, for prevention of generation of odor at the time of the catalyst preparation and recovery and reuse of these compounds. The use rate of such a nitrogen-containing heterocyclic compound can be suitably selected within a range of 1–50% by weight based on the weight of oxides of the raw materials containing the catalyst-constituting elements.

The raw materials containing the catalyst-constituting elements are subject to no particular limitation, but any of those generally used for preparation of heteropolyacid catalysts may be used. For example, as molybdenum material, ammonium molybdates such as ammonium paramolybdate, ammonium dimolybdate and the like, molybdic acid, molybdenum trioxide, etc. can be used. As vanadium material, vanadium pentoxide, ammonium metavanadate, sodium metavanadate, vanadyl oxalate, vanadyl sulfate and the like can be used. As phosphorus material orthophosphoric acid, disodium hydrogenphosphate, ammonium phosphate and the like can be used. It is also permissible to use a raw material containing more than one element, such as molybdophosphoric acid, molybdovanadophosphoric acid and the like.

As source for ammonium ion supply, ammonia or ammonium salts are useful. As examples of ammonium salts, besides ammonium nitrate, ammonium carbonate, ammonium hydrogencarbonate, ammonium acetate and the like, those raw materials containing catalyst-constituting elements, such as ammonium molybdate, ammonium phosphate, ammonium metavanadate and the like may be named.

As supply source of nitrate anions, nitric acid, ammonium nitrate or nitric acid salts which serve as the raw materials containing catalyst-constituting elements may be named.

According to the method of the invention, in preparing an aqueous solution or dispersion of such raw materials containing the catalyst-constituting elements and heterocyclic compound by mixing said raw materials containing the catalyst-constituting elements with a nitrogen-containing heterocyclic compound in the presence of water, the composition of said aqueous solution or dispersion is so adjusted that (1) nitrate anions and ammonium ions should be present in the solution or dispersion; (2) the ammonium ion content should not exceed 1.7 mols per mol of the nitrate anion content (i.e., 0<ammonium ions/nitrate anions$\leq$1.7 in terms of molar ratio); and (3) the ammonium ion content should not exceed 10 mols per 12 mols of molybdenum atom content (i.e., 0<ammonium ions/12 molybdenum atoms$\leq$10 in terms of molar ratio).

The molar ratio between the ammonium ion content and nitrate anion content is more than 0 but not more than 1.7, preferably 0.1–1.5. When this value exceeds 1.7, the intended heteropolyacid catalyst cannot be obtained. Where no ammonium ion is contained, moldability is objectionably impaired. The ammonium ion content per 12 mols of molybdenum atoms is more than 0 but not more than 10, preferably 0.2–9, inter alia, 2–9. When this value exceeds 10, the intended heteropolyacid catalyst cannot be obtained.

For adjusting the molar ratio of ammonium ions/nitrate anions and that of ammonium ions/molybdenum to fall within the above-specified ranges, the raw materials containing the catalyst-constituting elements and supply source of nitrate anions or that of ammonium ions are to be suitably selected. For example, where ammonium paramolybdate, $(NH_4)_6[Mo_7O_{24}] \cdot 4H_2O$, is used as the molybdenum material, the ammonium ion content per 12 molybdenum atoms of said raw material itself is 10.29. Therefore, by concurrent use of other molybdenum materials such as molybdenum trioxide, molybdophosphoric acid and the like which do not contain ammonium ions, the ammonium ion content as a whole can be adjusted to fall within the specified range.

The reason why the intended heteropolyacid catalyst is obtained when the nitrate anion content and ammonium ion content are adjusted to the specified ranges is not yet clear. Presumably, the adjustment, acting in concert with the presence of a nitrogen-containing heterocyclic compound, renders the pH, viscosity and particle size in the slurried condition, or reactivity of the involved substances, their oxidation-reduction conditions, etc. accompanying thereto, very favorable.

The aqueous solution or dispersion obtained as above is then concentrated under heating and stirring, and the resulting concentrate is subsequently dried and calcined. The drying and calcining conditions of the concentrate are subject to no critical limitations, but those generally used in preparation of heteropolyacid catalysts can be used. More specifically, the concentrate is dried at temperatures ranging 100–300° C., and normally after being molded, calcined at temperatures ranging 200–600° C. The calcining may also be carried out in such a manner that it is conducted at 200–600° C. in an inert gas such as gaseous nitrogen and then further at 100–400° C. in the air.

Conditions for carrying out the vapor phase oxidation or oxidehydrogenation reaction of methacrolein, isobutyl aldehyde and/or isobutyric acid in the presence of the catalyst of the present invention are not critical but those generally used for this type of reaction may be adopted. For example, in vapor phase oxidation of methacrolein, a gaseous mixture of 1–10 volume % of methacrolein, 1–10 volume times thereof of molecular oxygen and inert gas such as nitrogen, carbon dioxide steam and the like (of those, steam is particularly advantageous because it inhibits formation of side-products and improves yield of the object product) as diluent, is introduced onto the catalyst at a temperature within a range of 200–400° C. and under a pressure ranging from normal to 1 MPa, at a space velocity of 100–5,000 h$^{-1}$ (STP). The starting methacrolein is not necessarily required to be pure. For example, a methacrolein-containing gas obtained from a catalytic reaction of isobutylene or tertiary butanol may be used as the methacrolein. This embodiment is particularly recommendable for an industrial process.

Effect of the Invention

According to the invention, a heteropolyacid catalyst excelling in performance, life and strength can be prepared, and by using this heteropolyacid catalyst, methacrylic acid can be produced at high yield.

EXAMPLES

Hereinafter the present invention is explained more specifically, referring to working Examples, it being understood that the invention is not limited thereto. In the following Examples and Comparative Examples, the conversion, selectivity and one-pass yield have the following definitions.

Conversion (mol %)=(mol number of reacted methacrolein)/(mol number of supplied methacrolein)×100

Selectivity (mol %)=(mol number of formed methacrylic acid)/(mol number of reacted methacrolein)×100

One-pass yield (mol %)=(mol number of formed methacrylic acid)/(mol number of supplied methacrolein)×100

EXAMPLE 1

To 2,800 ml of 60° C. water, 900 g of ammonium paramolybdate, 273 g of molybdenum trioxide and 68.2 g of ammonium matavanadate were added and stirred, followed by further addition of 280 g of pyridine and 87.4 g of phosphoric acid (85% by weight), and a solution of 400 g of nitric acid (65% by weight), 136.4 g of cesium nitrate and 14.1 g of copper nitrate as dissolved in 1,000 ml of water, by the order stated, under continual stirring. Whereby an aqueous mixture containing pyridine, nitrate anions and ammonium ions was obtained, the ammonium ions/nitrate anions (molar ratio) being 1.00 and the ammonium ions/12 molybdenum atoms (molar ratio) being 8.49. This aqueous mixture was concentrated under heating and stirring, and the resulting clay-like substance was molded into a columns of each 5 mm in diameter and 6 mm in height, which were dried at 250° C. and calcined in a gaseous nitrogen stream at 430° C. for 4 hours, and then in an air stream at 400° C. for 2 hours. Thus obtained catalyst contained the metal elements excluding oxygen at the atomic ratios of: P:Mo:V:Cu:Cs= 1.3:12:1:0.1:1.2. Upon X-ray diffraction (per cathode Cu-Kα) measurement, the catalyst was found to have a composition composed mainly of molybdovanadophosphoric acid and its partial metal salt.

Fifty (50) ml of above catalyst was filled in a U-shaped stainless steel tube of 25 mm in inner diameter. The tube was immersed in a molten salt bath of 280° C., and into which a gaseous mixture of the following composition, which was obtained by vapor phase oxidation of isobutylene in the presence of a multi-elementary catalyst composed of oxides of molybdenum, cobalt, bismuth, iron and the like, was introduced:

| | |
|---|---|
| methacrolein | 3.5 volume % |
| isobutylene | 0.04 volume % |
| methacrylic acid + acetic acid | 0.24 volume % |
| steam | 20.0 volume % |
| oxygen | 9.0 volume % |
| inert gases mainly of nitrogen and carbon dioxide | 67.22 volume % |

The reaction was carried out under the conditions of: temperature, 280° C. and space velocity, 1,000 h$^{-1}$ (STP).

The results are shown in Table 1, together with the ammonium ions/12 molybdenum atoms ($NH_4/Mo_{12}$) and the ammonium ions/nitrate anions ($NH_4/NO_3$) in the aqueous mixture, and the BET specific surface area of the catalyst.

Example 2

Example 1 was repeated except that the amount of the ammonium paramolybdate was changed to 600 g and that of the molybdenum trioxide, to 518 g. The results are shown in Table 1.

EXAMPLE 3

Example 1 was repeated except that the amount of the ammonium paramolybdate was changed to 150 g, and that of the molybdenum trioxide, to 884 g. The results are shown in Table 1.

EXAMPLE 4

Example 1 was repeated except that the amount of the nitric acid was changed from 400 g to 250 g. The results are shown in Table 1.

Example 5

Example 1 was repeated except that the amount of the nitric acid was changed from 400 g to 750 g. The results are shown in Table 1.

Example 6

Example 1 was repeated except that the pyridine was replaced with the same amount of piperidine. The results are shown in Table 1.

Example 7

Example 1 was repeated except that the pyridine was replaced with the same amount of piperazine. The results are shown in Table 1.

Example 8

Example 1 was repeated except that no ammonium paramolybdate was used, the amount of molybdenum trioxide was changed to 1007 g and 265 g of aqueous ammonia (28% by weight) was added simultaneously with the pyridine. The results are shown in Table 1.

Comparative Example 1

Example 1 was repeated except that the amount of the ammonium paramolybdate was changed to 1236 g and that no ammonium trioxide was used. The results are shown in Table 1.

Comparative Example 2

Example 1 was repeated except that the amount of the nitric acid was changed from 400 g to 150 g. The results are shown in Table 1.

TABLE 1

| | $NH_4/Mo_{12}$ molar ratio | $NH_4/NO_3$ molar ratio | Methacrolein conversion (mol %) | Methacrylic acid selectivity (mol %) | Methacrylic acid one-pass yield (mol %) | BET specific surface area (m$^2$/g) |
|---|---|---|---|---|---|---|
| Example 1 | 8.49 | 1.00 | 82.1 | 82.0 | 67.3 | 5.2 |
| Example 2 | 5.99 | 0.71 | 82.5 | 81.9 | 67.6 | 5.1 |
| Example 3 | 2.25 | 0.26 | 81.5 | 82.6 | 67.3 | 5.2 |
| Example 4 | 8.49 | 1.46 | 82.2 | 81.8 | 67.2 | 5.1 |
| Example 5 | 8.49 | 0.58 | 82.3 | 82.0 | 67.5 | 5.3 |
| Example 6 | 8.49 | 1.00 | 81.5 | 82.1 | 66.9 | 5.0 |
| Example 7 | 8.49 | 1.00 | 82.4 | 81.6 | 67.2 | 5.1 |
| Example 8 | 8.49 | 1.00 | 82.0 | 82.0 | 67.2 | 5.2 |
| Comparative Example 1 | 11.28 | 0.75 | 79.6 | 79.3 | 63.1 | 4.9 |
| Comparative Example 2 | 8.49 | 2.09 | 80.5 | 78.3 | 63.0 | 5.0 |

What is claimed is:

1. A method for preparing a heteropolyacid catalyst containing a heteropolyacid composed of molybdophosphoric acid and/or molybdovanadophosphoric acid, or a salt of the heteropolyacid, in the presence of a nitrogen-containing heterocyclic compound, said method comprising preparing an aqueous solution or aqueous dispersion which (1) contains the nitrogen-containing heterocyclic compound, nitrate anions and ammonium ions, (2) the ammonium ion content not exceeding 1.7 mols per mol of the nitrate anion content, and (3) the ammonium ion content not exceeding 10 mols per 12 mols of the molybdenum atom content, by mixing raw materials containing the catalyst-constituting elements with the nitrogen-containing heterocyclic compound in the presence of water, drying and calcining the same.

2. A method according to claim 1, in which the heteropolyacid catalyst obtained is expressed by a general formula, $$P_a Mo_b V_c X_d O_x$$

(wherein P, Mo and V are phosphorus, molybdenum and vanadium, respectively; X represents at least one metal element capable of forming a heteropolyacid salt; O is oxygen; a, b, c, d and x signify atomic ratios of P, Mo, V, X and O, respectively, where b is 12, a is 0.1–3, c is 0–6 and d is 0.05–5, and x is a numerical value determined by valency of each element).

3. A method according to claim 1, in which the nitrogen-containing heterocyclic compound is selected from the group consisting of pyridine, piperidine, piperazine, pyrimidine, quinoline, isoquinoline and their alkyl derivatives.

4. A method according to claim 1, in which a source for supplying ammonium ions and/or a source for supplying nitrate anions is mixed with raw materials containing the catalyst-constituting elements and a nitrogen-containing heterocyclic compound in the presence of water.

5. A method according to claim 4, in which the ammonium ion-supplying source is ammonia or an ammonium salt.

6. A method according to claim 5, in which the ammonium salt is ammonium nitrate, ammonium carbonate, ammonium hydrogencarbonate or ammonium acetate.

7. A method according to claim 4, in which the nitrate anion-supplying source is nitric acid or ammonium nitrate.

8. A method according to claim 1, in which a molybdenum compound not containing ammonium ions; or a molybdenum compound not containing ammonium ions and a molybdenum compound containing ammonium ions; are used as the raw material(s) containing the catalyst-constituting element(s).

9. A method according to claim 1, in which the calcination is conducted at a temperature within a range of 200–600° C.

10. A method according to claim 1, in which the calcination is conducted in an inert gas at a temperature within a range of 200–600° C. and further at 100–400° C. in the air.

* * * * *